United States Patent
Koch et al.

(10) Patent No.: US 6,512,126 B2
(45) Date of Patent: Jan. 28, 2003

(54) PROCESS FOR PREPARING MINT LACTONE

(75) Inventors: Oskar Koch, Goettingen (DE); Walter Kuhn, Holzminden (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 10/001,592

(22) Filed: Oct. 19, 2001

(65) Prior Publication Data

US 2002/0077489 A1 Jun. 20, 2002

(30) Foreign Application Priority Data

Oct. 25, 2000 (DE) ......................................... 100 52 803

(51) Int. Cl.⁷ ........................................... C07D 307/79
(52) U.S. Cl. ..................................................... 549/307
(58) Field of Search ......................................... 549/307

(56) References Cited

PUBLICATIONS

Foote, Christopher S. et al: "Photosensitized oxygenation of alkyl–substituted furans" Tetrahedron, (1967), 23(6), 2583–99, XP001061562 Seite 2591, Zeile 1–10.

Tanyeli, Cihangir et al: " A facile synthesis of (.+−.)–mint-lactone" Synth. Commun. (1997), 27(19), 3471–3476, XP001061557 Seite 3472 scheme 1.

Tsuboi, Sadao et al: " New synthesis of (.+−.)–menthofuran" J. Org. Chem. (1980), 45(8), 1517–20, XP001061503 seite 1518 scheme 1.

Hirsch, Jerry A. et al: "Hydrolysis of.alpha.,.alpha.–d-imethoxydihydromenthofuran" J. Org. Chem. (1967), 32(9), 2915–16, XP001061502 das ganze Dokument.

Patent Abstracts of Japan vol. 018, No. 075 (C–1163), Feb. 8, 1994 & JP 05 286961 A (Toyotama Koryo KK), Nov. 2., 1993 Zusammenfassung.

Yoshida Toshio: Agric. Biol. Chem., Bd. 44, Nr. 7, 1980, Seiten 1535–1543, XP001061594 in der Anmeldung erwähnt Abbildung 8.

Tetrahedron (month unavailable) 1967, p. 2601–2608, S.C. Foote, M.T. Wuesthoff and I.G. Burstain, Structure and Stereochemistry of the Ketoacids Derived from Menthofuran Photoperoxide.

*Primary Examiner*—T. A. Solola
(74) *Attorney, Agent, or Firm*—Joseph C. Gil; Noland J. Cheung

(57) ABSTRACT

Mint lactone can be prepared by hydrogenating hydroxymenthofurolactone to give the intermediate dihydrohydroxymenthofurolactone with the subsequent elimination of water.

6 Claims, No Drawings

PROCESS FOR PREPARING MINT LACTONE

FIELD OF THE INVENTION

The present invention relates to a process for preparing 3,6-dimethyl-5,6,7,7a-tetrahydro-4H-benzofuran-2-one ("mint lactone") from hydroxymenthofurolactone. Mint lactone is an important constituent of the peppermint plant and is, therefore, essential for the preparation of nature-identical mint flavorings.

BACKGROUND OF THE INVENTION

Mint lactone (II) is customarily synthesized from hydroxymenthofurolactone (I) by reaction with the reducing agent sodium borohydride.

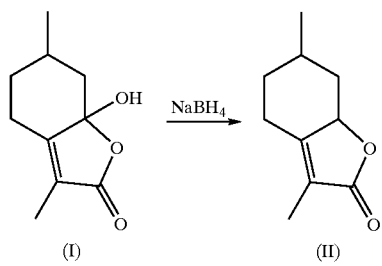

However, the process is uneconomical in the reduction stage because of the high price of the reducing agent sodium boranate. And due to the hydrogen formed in the process, appropriate safety precautions need to be taken. For this reason, the metering of the reducing agent is extended over a long period of 7 hours in order to keep the content of elemental hydrogen as low as possible in the exhaust air. This inevitably causes long reaction times and high costs.

It is therefore desirable to employ an improved and cheaper process for preparing mint lactone.

A possible alternative to the abovementioned process is the hydrogenation of dehydromenthofurolactone (III), which is described in the Journal of Agric. Biol. Chem. 44(7), 1535 (1980) on a laboratory scale in the presence of platinum dioxide as catalyst. Dehydromenthofurolactone (III) is prepared by acid-catalyzed elimination of water from hydroxymenthofurolactone (I).

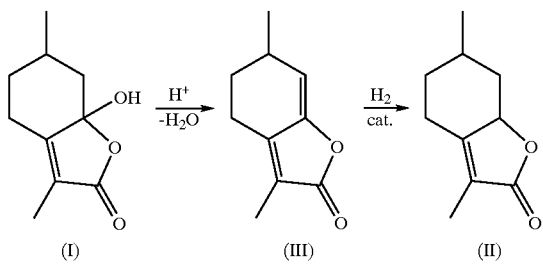

The yields of mint lactone reported there are less than 50% and were, thus, uneconomical.

In addition, Tetrahedron 23, 2601 (1967) discloses that, in the hydrogenation of hydroxymenthofurolactone (I) using a palladium catalyst in ethanol, an isomeric mixture of the ketoacids IV below is formed. The reaction has also only been carried out on a laboratory scale.

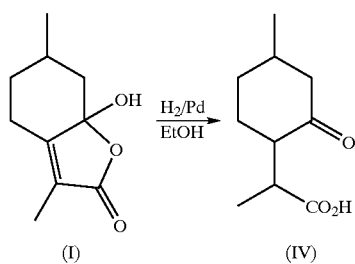

In addition, Tetrahedron 23, 2601 (1967) describes that treating these ketone acids IV with phosphorus pentoxide or potassium bisulphate leads to the unsaturated lactone V which is isomeric with mint lactone.

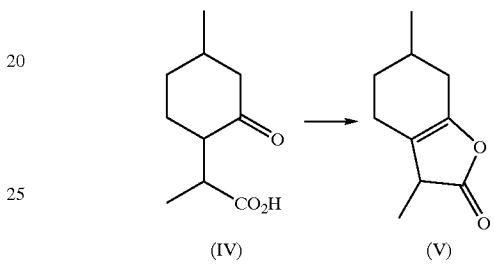

The solubility of hydroxymenthofurolactone (I) in ethanol, and also in other organic solvents, is extremely poor and thus an industrial hydrogenation, as described in Tetrahedron 23, 2601 (1967), is not practicable.

SUMMARY OF THE INVENTION

A process has been found for preparing mint lactone by hydrogenating hydroxymenthofurolactone to give the intermediate dihydrohydroxymenthofurolactone and subsequent elimination of water.

The inventive process can be described by the following reaction equation:

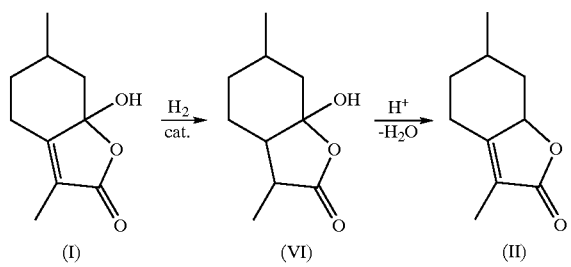

DETAILED DESCRIPTION OF THE INVENTION

Surprisingly, it is possible to hydrogenate solutions of hydroxymenthofurolactone (I) in dilute alkali metal hydroxide solution without problem. This produces in high yields a mixture of the isomeric ketoacids IV which are in equilibrium with dihydrohydroxymenthofurolactone (VI).

It is also surprising that the intermediate VI which forms after hydrogenation (equilibrium mixture between compounds IV and VI) does not proceed via acid-catalyzed elimination of water to the product V, but also leads to very good yields of mint lactone (II).

It is also advantageous that it is not necessary to work up the intermediate (IV/VI), as is generally performed by distillation or crystallization. The alkaline aqueous solution present from the hydrogenation is acidified using mineral acids and extracted with a water-immiscible organic solvent, for example toluene. By adding catalytic amounts of a mineral acid to this organic phase, the eliminated water is removed as an azeotrope. For this reason, water-immiscible organic solvents are preferred which simultaneously form an azeotrope with water.

For the hydrogenation by the inventive process, the hydroxymenthofurolactone is dissolved in an aqueous alkali metal hydroxide solution.

Aqueous alkali metal hydroxide solutions which may be mentioned by way of example are: aqueous alkali metal hydroxide solutions such as lithium hydroxide, sodium hydroxide or potassium hydroxide.

The concentration of the aqueous alkali metal hydroxide solution is generally in the concentration range from 1 to 80% by weight, preferably in the range from 2 to 20% by weight.

The concentration of the hydroxymenthofurolactone in the aqueous alkali metal hydroxide solution can vary within broad ranges. Concentrations of 10 to 60, preferably 20 to 50,% by weight are preferred. Suitable catalysts for the hydrogenation of hydroxymenthofurolactone (I) are the customary hydrogenation catalysts, such as noble metals such as platinum, palladium, rhodium, other transition metals such as molybdenum, tungsten, chromium, iron, cobalt, nickel, in each case individually or in a mixture.

The hydrogenation catalyst is preferably selected from platinum, palladium and their compounds. It can be used in the form of the metals, for example finely divided as platinum black or palladium black, or in the form of compounds of these metals, for example as metal salt or metal complex. All forms of the catalyst used can also be applied to supports.

Preferred catalysts comprise, for example, platinum compounds $PtO_2$, $H_2PtCl_6$, $PtCl_2$, $PtCl_4$, $PtBr_2$, $PtI_2$, $Pt(NH_3)NO_2)_2$, $Pt(NH_3)_4Cl_2$, $Pt(H_2NCH_2CH_2CH_2)_2Cl_2$, and the palladium compounds PdO, $PdSO_4$, $PdBr_2$, $PdCl_2$, $Pd(CH_3CO_2)_2Pd(NH_3)_4(NO_3)_2$, Pd(II) acetylacetonate and Pd(II) trifluoroacetate.

Suitable catalyst supports are industrially conventional catalyst supports, for example those based on carbon, element oxides, element carbides or element salts in various usage forms. Examples of element oxide catalyst supports are silicon dioxide (natural or synthetic silicic acids, quartz), aluminum oxide, aluminas, natural and synthetic aluminosilicates (zeolites), titanium dioxide (rutile, anatase), zirconium oxide or zinc oxide. Preferred element carbides and element salts include silicon carbide, aluminum phosphate, barium sulphate, calcium carbonate. They can be used both as chemically homogeneous pure substances and as a mixture. According to the present invention, suitable catalyst supports are materials both in pieces and in powder form.

The use of catalysts on supports is preferred. More preference is given to the use of platinum and palladium on supports, for example carbon.

The loading of the support with catalyst is preferably 0.1 to 15%, more preferably, 5 to 10% by weight, based on the total of support and catalyst, calculated as metal.

The catalyst is used in amounts of 0.001 to 5%, preferably 0.01 to 1% by weight, calculated as metal and based on hydroxymenthofurolactone (I).

Hydroxymenthofurolactone (I) can be hydrogenated with hydrogen at a pressure of 1 to 100, preferably 10 to 20 bars and at temperatures of 5 to 200, preferably 20–40° C.

The acid-catalyzed elimination of water by the inventive process is generally carried out in the presence of mineral acids.

In a preferred embodiment, for this purpose, extraction from the aqueous hydrogenation solution is carried out using a water-immiscible solvent that simultaneously forms an azeotrope with water, for example toluene or xylene. Preferably, a pH of about 1 is established during this extraction. For this, mineral acids, for example hydrochloric acid, sulfuric acid or phosphoric acid, are suitable.

Mint lactone is obtained in high purity by this process.

EXAMPLE 400 g (2.20 mol) of hydroxymenthofurolactone, dissolved in 1,000 g of sodium hydroxide solution, 10 percent, and 2.0 g of Pd/C are charged into an autoclave and hydrogenated at 20 bar and a temperature of 25–30° C. The reaction is terminated after 2 h.

After cooling to room temperature and separating off the catalyst, the pH of the filtrate is adjusted from 13 to 1 by adding 570 g of sulfuric acid, 30 percent. The oil phase settling out is extracted with 600 g of toluene. After phase separation, 5 g of sulfuric acid, concentrated, are added and the mixture is boiled under reflux for 3 h on a water separator, with approximately 60 g of water being separated. After cooling to room temperature, the organic phase is again washed with 200 g of water and then distilled on a 15 cm Vigreux column. 334 g of mint lactone having a purity of 99% are obtained. Yield over both stages is 91% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing mint lactone comprising the steps of hydrogenating hydroxymenthofurolactone to give the intermediate dihydrohydroxymenthofurolactone and subsequent eliminating the water.

2. A process according to claim 1, wherein hydrogenation takes place in an aqueous alkaline solution at a pH of 8–14.

3. A process according to claim 1, wherein hydrogenation takes place at a hydrogen pressure of 1–100 bar.

4. A process according to claim 1, wherein hydrogenation takes place at a temperature of 5–200° C.

5. A process according to claim 1, wherein hydrogenation takes place in the presence of platinum or palladium as catalyst.

6. A process according to claim 1, wherein the intermediate, after the hydrogenation, is extracted with a water-immiscible organic solvent which simultaneously forms an azeotrope with water.

* * * * *